(12) United States Patent
Hoffman

(10) Patent No.: US 8,852,288 B2
(45) Date of Patent: Oct. 7, 2014

(54) HIP PROSTHESIS

(75) Inventor: Erik Leonard Hoffman, Nuenen (NL)

(73) Assignee: Biomet UK Limited, South Wales (GB)

( * ) Notice: Subject to any disclaimer, the term of this patent is extended or adjusted under 35 U.S.C. 154(b) by 523 days.

(21) Appl. No.: 12/598,824

(22) PCT Filed: May 8, 2008

(86) PCT No.: PCT/NL2008/050276
§ 371 (c)(1),
(2), (4) Date: Mar. 31, 2010

(87) PCT Pub. No.: WO2008/140306
PCT Pub. Date: Nov. 20, 2008

(65) Prior Publication Data
US 2010/0198356 A1   Aug. 5, 2010

(30) Foreign Application Priority Data

May 9, 2007   (NL) ...................................... 2000639

(51) Int. Cl.
*A61F 2/36* (2006.01)
*A61F 2/30* (2006.01)
*A61F 2/46* (2006.01)

(52) U.S. Cl.
CPC ......... *A61F 2/36* (2013.01); *A61F 2002/30332* (2013.01); *A61F 2310/00544* (2013.01); *A61F 2002/4631* (2013.01); *A61F 2002/30589* (2013.01); *A61F 2/367* (2013.01); *A61F 2002/30827* (2013.01); *A61F 2/3601* (2013.01); *A61F 2220/0033* (2013.01); *A61F 2002/30738* (2013.01); *A61F 2002/30606* (2013.01); *A61F 2002/3625* (2013.01); *A61F 2/3662* (2013.01); *A61F 2002/3686* (2013.01); *A61F 2002/3631* (2013.01); *A61F 2310/00407* (2013.01); *A61F 2/30767* (2013.01); *A61F 2002/365* (2013.01)

USPC ................. 623/23.15; 623/22.11; 623/23.21; 623/23.29

(58) Field of Classification Search
USPC .......... 623/23.11–23.15, 23.19, 23.21–23.25, 623/23.29–23.31, 23.33–23.36
See application file for complete search history.

(56) References Cited

U.S. PATENT DOCUMENTS 3,228,393 A * 1/1966 Michele ..................... 623/23.15
4,658,808 A   4/1987 Link
(Continued)

FOREIGN PATENT DOCUMENTS

AU     2008251118 A1   11/2008
CA        2685933 A1   11/2008
(Continued)

OTHER PUBLICATIONS

International Search Report mailed Sep. 30, 2008 for PCT/NL2008/050276 claiming benefit of Netherlands (NL) 2000639 filed May 9, 2007.

(Continued)

*Primary Examiner* — David Isabella
*Assistant Examiner* — Yashita Sharma
(74) *Attorney, Agent, or Firm* — Harness, Dickey

(57) ABSTRACT

A hip prosthesis has an oblong plate with at one head end a mounting pin provided with a hinge ball, and at the opposite head end a fastening pin for fastening the hip prosthesis in a shaft of a bone. A first part of the plate extends on a first side of the mounting pin. The mounting pin forms an angle α smaller than 90 degrees with the first part of the plate and the tangent to the fastening pin at the location of the connection between the fastening pin and the first part of the plate forms an angle β greater than 90 degrees with the first part of the plate. In order to insert the hip prosthesis into a bone in a simple manner, the fastening pin includes a curved shape from the plate onwards in a direction to the first part of the plate.

18 Claims, 2 Drawing Sheets

(56) References Cited

U.S. PATENT DOCUMENTS

| | | | |
|---|---|---|---|
| 4,661,112 A | 4/1987 | Mueller | |
| 4,881,536 A | 11/1989 | Noble et al. | |
| 5,108,451 A * | 4/1992 | Forte | 623/22.41 |
| 5,314,489 A * | 5/1994 | Hoffman et al. | 623/23.25 |
| 5,549,698 A * | 8/1996 | Averill et al. | 623/22.22 |
| 6,132,468 A * | 10/2000 | Mansmann | 623/20.16 |
| 6,224,634 B1 * | 5/2001 | Keller | 623/23.11 |
| 6,332,896 B1 | 12/2001 | Hubbard et al. | |
| 6,652,591 B2 * | 11/2003 | Serbousek et al. | 623/23.31 |
| 6,695,884 B1 | 2/2004 | Townley | |
| 6,702,854 B1 * | 3/2004 | Cheal et al. | 623/22.42 |
| 7,494,509 B1 | 2/2009 | Hershberger et al. | |
| 7,875,083 B2 * | 1/2011 | Sudmann | 623/23.29 |
| 2003/0163202 A1 | 8/2003 | Lakin | |
| 2003/0187514 A1 | 10/2003 | McMinn | |
| 2008/0262629 A1 * | 10/2008 | Fonte | 623/23.15 |
| 2010/0198356 A1 | 8/2010 | Hoffman | |

FOREIGN PATENT DOCUMENTS

| | | |
|---|---|---|
| DE | 2331728 A1 | 1/1975 |
| DE | 2627569 | 12/1977 |
| DE | 4428099 | 2/1996 |
| EP | 0666069 A1 | 8/1995 |
| EP | 1175876 | 1/2002 |
| EP | 2155118 A1 | 2/2010 |
| FR | 2814060 | 3/2002 |
| JP | 2001518821 A | 10/2001 |
| JP | 2010525919 A | 7/2010 |
| NL | 2001566 C1 | 11/2008 |
| WO | WO 95/11640 | 5/1995 |
| WO | WO98/42279 | 10/1998 |
| WO | WO-2005117763 A2 | 12/2005 |
| WO | WO-2008140306 A1 | 11/2008 |

OTHER PUBLICATIONS

International Preliminary Report on Patentability and Written Opinion mailed Nov. 10, 2009 for PCT/NL2008/050276 claiming benefit of Netherlands (NL) 2000639 filed May 9, 2007.

Microplasty™ Hip Steams, Taperloc™ Microplasty™ Stem, Balance™ Microplasty™ Stem. Biomet® Orthopedics, Inc. Brochure (Jan. 2008) 8 pages.

Taperloc™ Hip System, Surgical Technique. Biomet® Orthopedics, Inc. Brochure (Jan. 2008) 11 pages.

European Communication Pursuant to Article 94(3) EPC mailed Dec. 11, 2013 for European Patent Application No. 08753759.3.

Japan Office Action mailed Sep. 24, 2013 for Japanese Patent Application No. 2010-507344.

* cited by examiner

HIP PROSTHESIS

FIELD OF THE INVENTION

The invention relates to a hip prosthesis, and more particularly to a hip prosthesis comprising a mounting pin having a hinge ball and a fastening pin for fastening the hip prosthesis in a shaft of a bone.

BACKGROUND OF THE INVENTION

A hip prosthesis of this type is disclosed in EP-A-1 205 163, which is hereby incorporated by reference in full. In this known hip prosthesis the fastening pin has a cylindrical shape and the fastening pin, after being introduced by surgery, extends along the axis of the neck portion of the bone, the part of the bone at which the ball part of the hip joint was present.

SUMMARY OF THE INVENTION

It is an object of the invention to provide a hip prosthesis which can be fixed in the bone in similar sturdy manner to the known hip prosthesis and with minimum invasive techniques, while the opening for introducing the hip prosthesis can be smaller than when the prior art hip prosthesis is introduced. For this purpose the hip prosthesis according to the invention is characterized in that the fastening pin, seen in longitudinal section, has a curved shape from the abutment surface onwards in a direction to the first part of the abutment surface, while the tangent to the hollow or concave side of the fastening pin at the location of the abutment surface forms an angle β that is greater than 90 degrees with the first part of the abutment surface. As a result of the fastening pin being of a curved nature and shorter than the prior art hip prosthesis, the hip prosthesis according to the invention can be introduced through a smaller opening than the prior art hip prosthesis.

An embodiment of the hip prosthesis according to the invention is characterized in that the angle β is between 100 and 120 degrees. The angle β is preferably equal to 110 degrees.

A further embodiment of the hip prosthesis according to the invention is characterized in that the angle α is between 40 and 70 degrees. The angle α is preferably between 50 and 60 degrees.

A still further embodiment of the hip prosthesis according to the invention is characterized in that the inner radius of curvature of the fastening pin is between 60 and 120 millimeters. The inner radius of curvature of the fastening pin being between 60 and 120 millimeters. The inner radius of curvature of the fastening pin is preferably between 75 and 100 millimeters.

The hip prosthesis according to the invention may be fixed in the bone in both uncemented and cemented fashion. An embodiment of the hip prosthesis according to the invention that is suitable for being fixed in both uncemented and cemented fashion is characterized in that the hip prosthesis preferably comprises an oblong plate which is present between the mounting pin and the fastening pin and runs parallel to the abutment surface, the mounting pin being present at one head end of the plate and the fastening pin being present at the opposite head end, the plate extending along the greater part of the circumference to beyond the fastening pin and forming a flange. The plate can then form one whole with the mounting pin and the fastening pin and can be a separate part and be introduced between mounting pin and fastening pin in detachable fashion or not.

Grooves are then preferably present in the fastening pin, which extend in longitudinal direction of the fastening pin starting from the free end of the fastening pin, while the ends of the grooves at the free end of the fastening pin are open. With uncemented application of the hip prosthesis the advantage of these grooves is that the growing of bone into the fastening pin is improved. With cemented application of the hip prosthesis the bone cement will fill up the grooves when the hip prosthesis is introduced into the shaft filled with bone sement, so that improved fixation is effected.

An embodiment of the hip prosthesis according to the invention, which is notably suitable for being fastened in uncemented fashion, is characterized in that the fastening pin of the hip prosthesis is provided with a foam coating. This coating is preferably in essence a tantalium or titanium coating. As a result, bone can grow into the coating, so that the hip prosthesis is fixed in the bone and peak tensions inside the bone at the location of the free end of the fastening pin are reduced or do not even occur at all.

A further embodiment of the hip prosthesis according to the invention is characterized in that at the location of or in close proximity to the first end the fastening pin is provided with a protruding ridge that extends over the entire circumference of the fastening pin. The advantage of this is that when the hip prosthesis is applied to a bone, a watertight sealing is obtained between the hip prosthesis and the bone at this spot, so that, in case of a bacterial infection, the bacteries are kept away from the bone.

The ridge is preferably provided with a watertight coating, so that an even better sealing is obtained.

BRIEF DESCRIPTION OF THE DRAWING FIGURES

The invention will be further described below in more detail with reference to embodiments of the hip prosthesis according to the invention represented in the drawing figures, in which.

DETAILED DESCRIPTION OF THE DRAWING FIGURES

Figure 1:
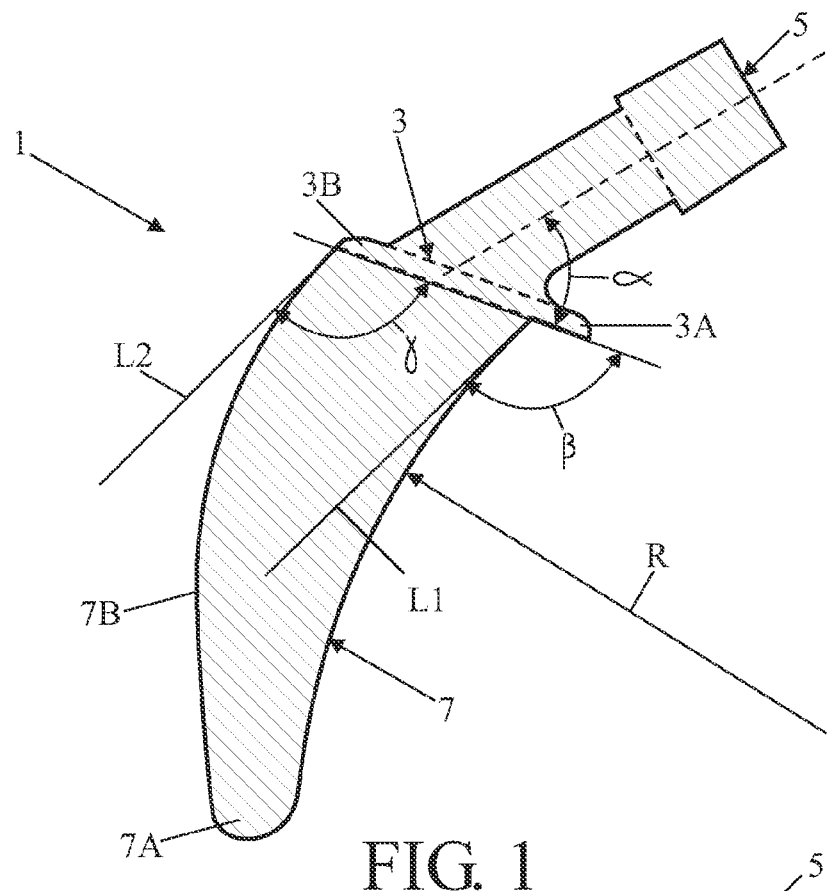
FIG. 1 shows a first embodiment of the hip prosthesis according to the invention of a plate in longitudinal section.

FIG. 1 shows a longitudinal section of an embodiment of the hip prosthesis according to the invention. The hip prosthesis 1 has an oblong plate 3 with at one head end a mounting pin 5 for mounting a hinge ball of a hip joint and at the opposite head end a fastening pin 7 for fastening the hip prosthesis in a shaft of a bone. A first part 3A of the plate here extends to a first side of the mounting pin 5 and a second part 3B of the plate extends to a second side of the mounting pin 5.

The mounting pin 5 forms an angle α smaller than 90 degrees with the first part 3A of the plate and the tangent L1 to the fastening pin 7 at the location of the connection of the fastening pin to the first part 3A of the plate forms an angle β greater than 90 degrees with the first part 3A of the plate. The tangent L2 to the fastening pin 7 at the location of the connection of the fastening pin to the second part 3B of the plate forms an angle γ with the second part 3B which is substantially equal to angle β.

The fastening pin 7 is curved from the plate 3 onwards in a direction to the first part 3A of the plate. Then the fastening pin 7, seen in longitudinal direction, tapers to the free end 7A.

At the location of the first part 3A of the plate, the plate protrudes beyond the fastening pin 7 and at the location of the second part 3B of the plate the end of the plate abuts on the outer wall 7B of the fastening pin. The plate 3, mounting pin 5 and fastening pin 7 are manufactured as one whole.

Preferably there are various embodiments of the hip prosthesis of which the angle α and the inner radius of curvature R of the fastening pin 7 are different from each other. Depending on the shape of the bone in which the hip prosthesis is introduced, there may be chosen for the hip prosthesis that fits best. In all these embodiments the angle α is between 50 and 60 degrees and the radius of curvature R is between 75 and 100 millimeters. In all these embodiments the angle β is equal to 110 degrees.

Figure 2:
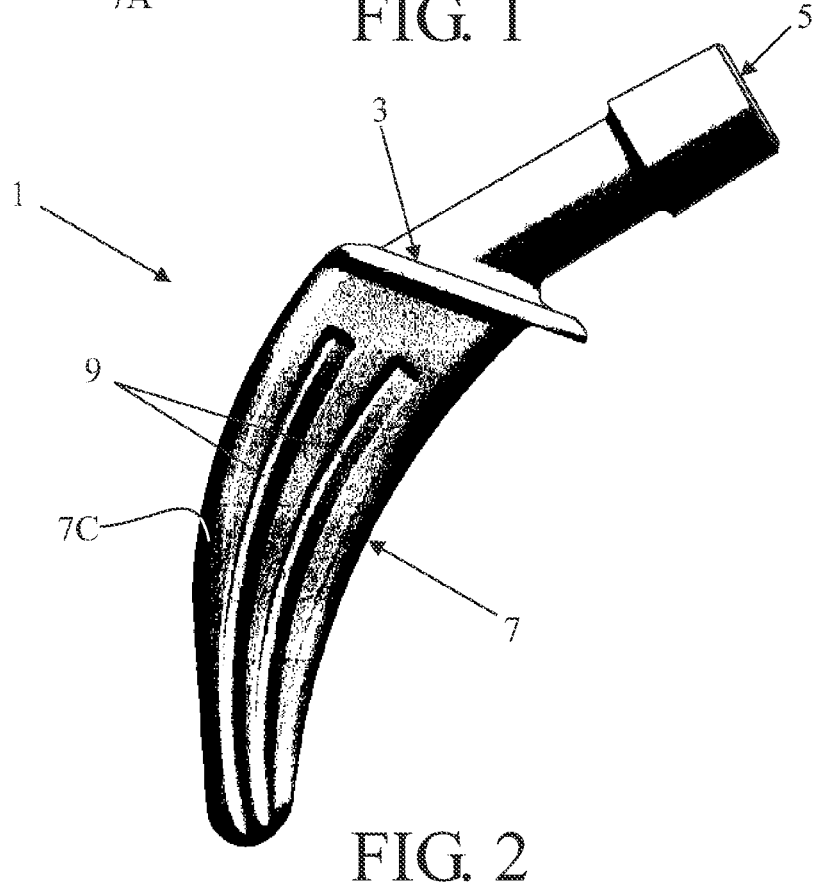
FIG. 2 shows a perspective view of the hip prosthesis represented in FIG. 1.
Figure 3:
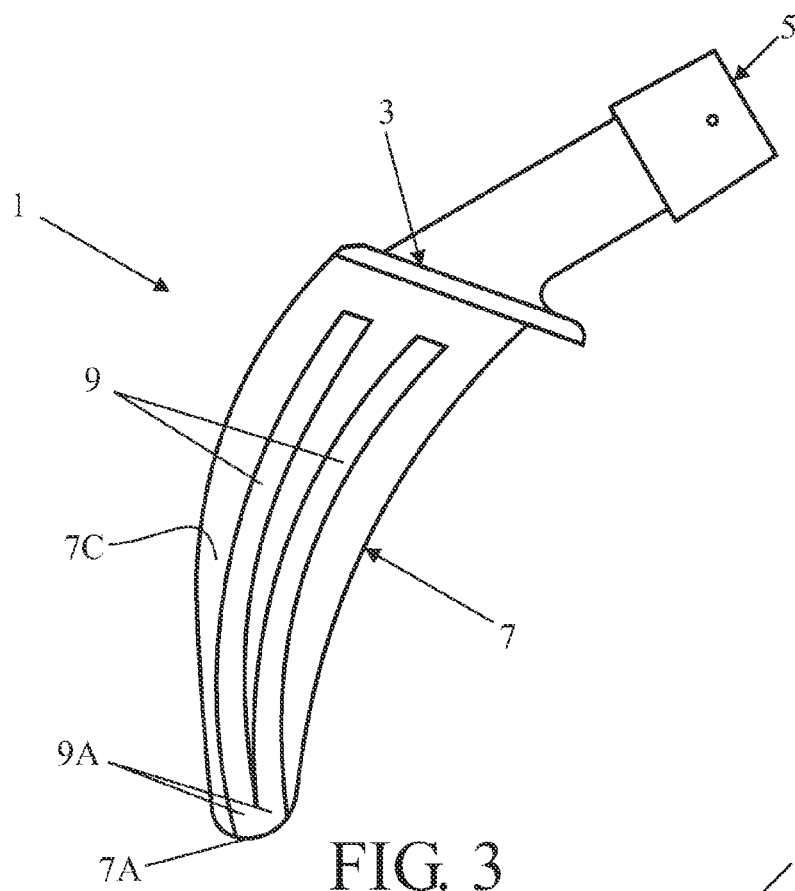
FIG. 3 shows a side view of the hip prosthesis represented in FIG. 1.

In FIG. 2 the hip prosthesis 1 is shown in perspective view for clarity. The hip prosthesis 1 can be fixed in the shaft of a bone with both bone cement and in uncemented fashion. The side walls 7C of the fastening pin 7 are provided with grooves 9, so that in the case of cemented fixation the bone cement can better bond to the fastening pin. The grooves extend from the free end 7A in longitudinal direction of the fastening pin 7. At the location of the free end 7A the ends of the grooves 9 are open, so that when the hip prosthesis is inserted into the shaft of the bone the bone cement can flow better into the grooves 9. In FIG. 3, in which a side view is shown of the hip prosthesis 1, it is clearly noticeable that the ends 9A of the grooves 9 are open.

Figure 4:
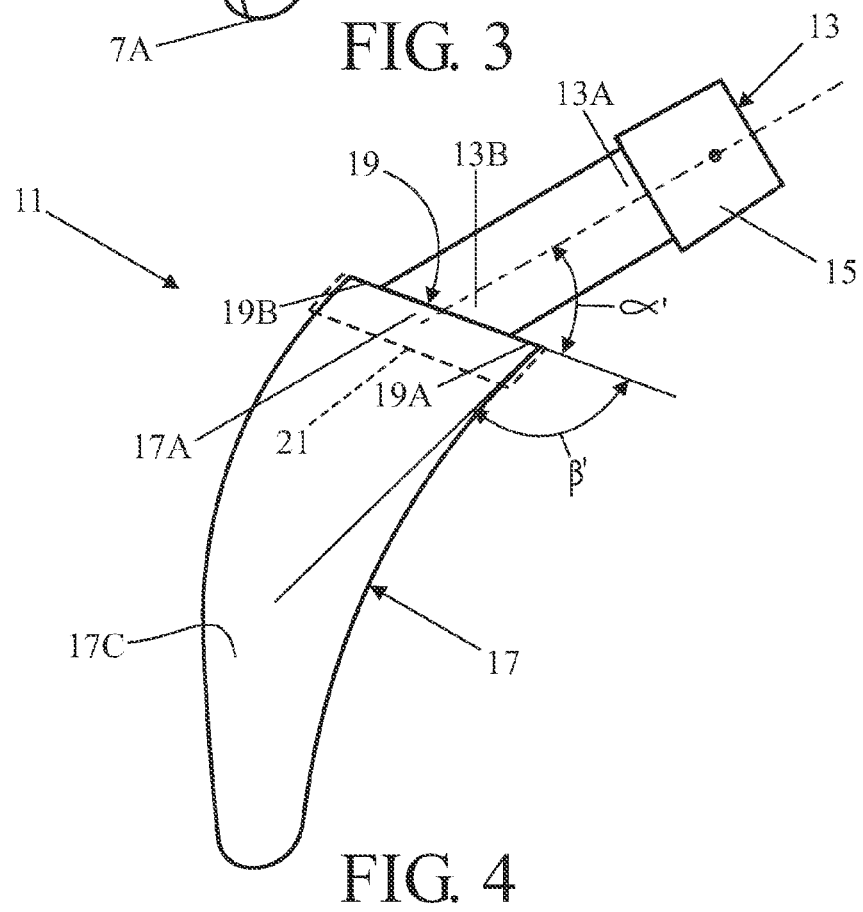
FIG. 4 shows a side view of a second, flangeless embodiment of the hip prosthesis according to the invention.

FIG. 4 shows a side view of a second embodiment of the hip prosthesis according to the invention. This hip prosthesis 11 is intended to be inserted without bone cement into the shaft of a bone. The hip prosthesis does not have a plate, at a first end 13A of the mounting pin 13 there being provided a cone 15 for mounting a hinge ball for a hip joint. The second end 13B of the mounting pin is directly fastened to a first end 17A of the fastening pin 17. This end is provided with an abutment surface 19 of which a first part 19A, seen in side view, extends to a first side of the mounting pin and a second part 19B of the abutment surface extends to a second side of the mounting pin. The mounting pin 13, seen in side view, forms an angle α' smaller than 90 degrees with the first part 19A of the abutment surface, and the tangent L to the hollow side of the fastening pin at the location of the abutment surface 19 forms and angle β' greater than 90 degrees with the first part 19A of the abutment surface.

In order to obtain a proper bonding of the hip prosthesis in the bone the surface 17C of the fastening pin 17 has a foam coating made of tantalium or titanium so as to enable bone growth. In the proximity of the first end 17A the fastening pin 17 may have a protruding ridge 21 that is provided with a conventional watertight coating. The advantage of this is that when the hip prosthesis is inserted into a bone a watertight sealing is obtained between the hip prosthesis and the bone at this spot, so that in case of a bacterial infection, the bacteria are kept away from the bone.

Albeit the invention has been elucidated in the foregoing with reference to the drawing figures, it should be set out that the invention is not by any manner or means restricted to the embodiments shown in the drawing figures. The invention also extends to any embodiments deviating from the embodiments shown in the drawing figures within the spirit and scope defined by the claims. For example, the protruding ridge in the embodiment shown in drawing FIG. 4 is not necessary if the fastening pin in lieu of being provided with a non-watertight foam coating is provided with a conventional watertight coating. In that case the ridge may thus be omitted.

What is claimed is:

1. A hip prosthesis comprising:
   a mounting pin portion extending from a first end to a second end, wherein the first end is configured to couple with a hinge ball, wherein the mounting pin extends along a pin axis from the first end to the second end;
   a fastening pin extending from near the second end of the mounting pin to a fastening pin terminal end, the fastening pin having a first side and an opposed second side, both the first side and the second side extending between a third concave side and an opposed fourth side;
   a plate extending from a first mounting pin side of the mounting pin to a second mounting pin side of the mounting pin, wherein the first mounting pin side is adjacent the third concave side; wherein the plate forms a first angle with the pin axis of the mounting pin near the first mounting pin side that is between 40 degrees and 70 degrees;
   wherein the plate forms a second angle with a tangent of the fastening pin near the third concave side of the fastening pin;
   wherein the fastening pin is configured to fasten the hip prosthesis in a shaft of a bone;
   wherein the first side and the second side both have a plurality of longitudinally extending grooves formed therein.

2. The hip prosthesis of claim 1, further comprising:
   an abutment surface at the second end of the mounting pin;
   wherein the third concave side of the fastening pin defines a first radius from the abutment surface to the fastening pin terminal end.

3. The hip prosthesis of claim 1, wherein the plate forms a third angle with a tangent of the fastening pin near the fourth side of the fastening pin.

4. The hip prosthesis of claim 3, wherein the second angle and the third angle are substantially equal.

5. The hip prosthesis of claim 4, wherein the first angle is less than the second angle.

6. The hip prosthesis of claim 3, wherein at least one of the second angle and the third angle is 110 degrees.

7. The hip prosthesis of claim 3, wherein at least one of the second angle and the third angle is between 100 degrees and 120 degrees.

8. The hip prosthesis of claim 1, wherein the first angle is less than the second angle.

9. The hip prosthesis of claim 8, wherein the first angle is between 50 degrees and 60 degrees.

10. The hip prosthesis of claim 9, wherein the third concave side of the fastening pin includes a radius between 75 millimeters and 100 millimeters.

11. The hip prosthesis of claim 9, wherein the third concave side of the fastening pin includes a radius between 60 millimeters and 120 millimeters.

12. A hip prosthesis comprising: a mounting pin portion extending from a first end to a second end, wherein the first end is configured to couple with a hinge ball, wherein the mounting pin extends along a pin axis from the first end to the second end;
   a fastening pin extending from near the second end of the mounting pin to a fastening pin terminal end, the fastening pin having a first side and an opposed second side, both the first side and the second side extending between a third concave side and an opposed fourth side;
   a plate extending from a first mounting pin side of the mounting pin to a second mounting pin side of the mounting pin, wherein the first mounting pin side is adjacent the third concave side and the plate includes an abutment surface for contacting a bone surface;

wherein the plate forms a first angle with the pin axis of the mounting pin near the first mounting pin side that is between 50 degrees and 70 degrees;

wherein the plate forms a second angle with a tangent of the fastening pin near the third concave side of the fastening pin that is between 100 degrees and 120 degrees;

wherein the fastening pin is configured to fasten the hip prosthesis in a shaft of a bone;

wherein the first side and the second side both have a plurality of longitudinally extending grooves formed therein.

13. The hip prosthesis of claim 12, wherein the second angle is 110 degrees.

14. The hip prosthesis of claim 13, wherein the fastening pin further includes a radius of the third concave side between 60 millimeters to 120 millimeters.

15. The hip prosthesis of claim 14, wherein the plurality of grooves includes at least a first two grooves on the first side and a second two grooves on the second side;

wherein both the first two grooves and the second two grooves extend from a free end of the fastening pin and terminate before the plate.

16. The hip prosthesis of claim 15, further includes a foam coating.

17. A hip prosthesis comprising: a mounting pin portion extending from a first end to a second end, wherein the first end is configured to couple with a hinge ball, wherein the mounting pin extends along a pin axis from the first end to the second end;

a fastening pin extending a length of between 120 millimeters to 240 millimeters from near the second end of the mounting pin to a fastening pin terminal end, the fastening pin having a first side and an opposed second side, both the first side and the second side extending between a third concave side and an opposed fourth side;

a plate extending from a first mounting pin side of the mounting pin to a second mounting pin side of the mounting pin, wherein the first mounting pin side is adjacent the third concave side and the plate includes an abutment surface for contacting a bone surface;

wherein the plate forms a first angle with the pin axis of the mounting pin near the first mounting pin side that is between 50 degrees and 70 degrees;

wherein the plate forms a second angle with a tangent of the fastening pin near the third concave side of the fastening pin that is 110 degrees;

wherein the fastening pin is configured to fasten the hip prosthesis in a shaft of a bone.

18. The hip prosthesis of claim 17, further comprising:

at least a first two grooves on the first side of the fastening pin and a second two grooves on the second side of the fastening pin;

wherein both the first two grooves and the second two grooves extend from a free end of the fastening pin and terminate before the plate.

* * * * *